(12) United States Patent
Gerondale

(10) Patent No.: US 8,403,176 B2
(45) Date of Patent: Mar. 26, 2013

(54) CONTROLLED DROP DISPENSING CONTAINER

(75) Inventor: Scott J. Gerondale, Mission Viejo, CA (US)

(73) Assignee: Allergan, Inc., Irvine, CA (US)

( * ) Notice: Subject to any disclaimer, the term of this patent is extended or adjusted under 35 U.S.C. 154(b) by 2301 days.

(21) Appl. No.: 10/349,572

(22) Filed: Jan. 22, 2003

(65) Prior Publication Data

US 2004/0140319 A1  Jul. 22, 2004

(51) Int. Cl.
*B65D 47/18* (2006.01)
(52) U.S. Cl. ............ 222/1; 222/215; 222/420; 428/36.6
(58) Field of Classification Search ................ 222/1, 92, 222/107, 153.07, 420, 421, 206, 212, 215; 428/36.6
See application file for complete search history.

(56) References Cited

U.S. PATENT DOCUMENTS

| | | | | |
|---|---|---|---|---|
| 2,874,881 A | * | 2/1959 | Stull | 222/421 |
| 4,257,536 A | | 3/1981 | Hilmar | 222/107 |
| 4,551,371 A | * | 11/1985 | Eckstein | 222/92 |
| 4,685,591 A | * | 8/1987 | Schaefer et al. | 222/107 |
| 5,221,017 A | * | 6/1993 | Cistone et al. | 215/235 |
| 5,480,067 A | * | 1/1996 | Sedlmeier | 222/107 |
| 5,588,559 A | * | 12/1996 | Mas et al. | 222/92 |
| 5,799,837 A | | 9/1998 | Firestone et al. | 222/215 |
| 5,804,270 A | | 9/1998 | Kawamura et al. | 428/36.92 |
| 6,000,578 A | * | 12/1999 | Boissay | 222/83 |
| 6,076,709 A | | 6/2000 | Wilner | 222/212 |
| 2001/0050291 A1 | * | 12/2001 | Jud et al. | 222/107 |
| 2002/0153386 A1 | | 10/2002 | Uetake et al. | 222/1 |

FOREIGN PATENT DOCUMENTS

EP  0 425 264 A1  10/1990

* cited by examiner

*Primary Examiner* — Kevin P Shaver
(74) *Attorney, Agent, or Firm* — Linda Fox; Stephen Donovan; Debra Condino

(57) ABSTRACT

The present invention relates to packaging materials for ophthalmic solutions. Difficulties with water loss in standard ophthalmic bottles are overcome in the controlled drop dispensing container of the present invention. This controlled drop dispensing container comprises a dispensing tip, a laminate tube 15, and a shoulder connecting the laminate tube 15 to the dispensing tip 7. The dispensing tip 7 comprises an inner orifice having a diameter sufficiently small to restrict flow of liquid contents of the tube to the desired level, an outer orifice 9 having a diameter sufficiently large to form a drop of the desired size from the liquid contents of the tube, where fluid communication exists between the inner orifice and the outer orifice 9. The laminate tube 15 comprises an outer polymeric layer 10, an optional first tie layer 11, a middle barrier layer 12, an optional second tie layer 13, an inner polymeric layer 14. Preferably, the controlled drop dispensing container 1 also comprises a cap 4 and a reusable seal 3 between the cap 4 and the dispensing tip 7. In another preferred embodiment of the invention, the cap 4 also comprises a tamper evident tear strip 5.

13 Claims, 1 Drawing Sheet

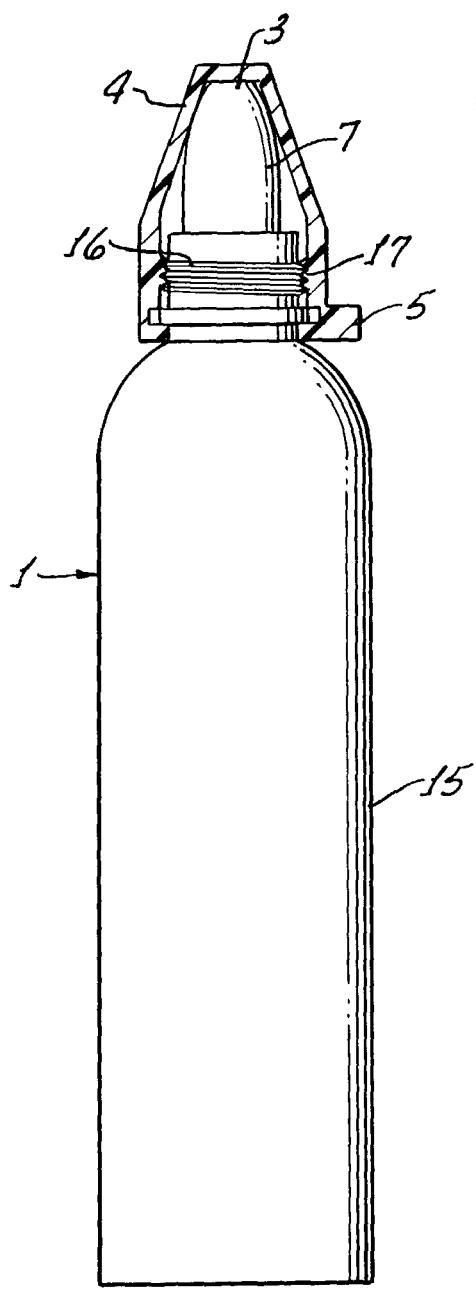
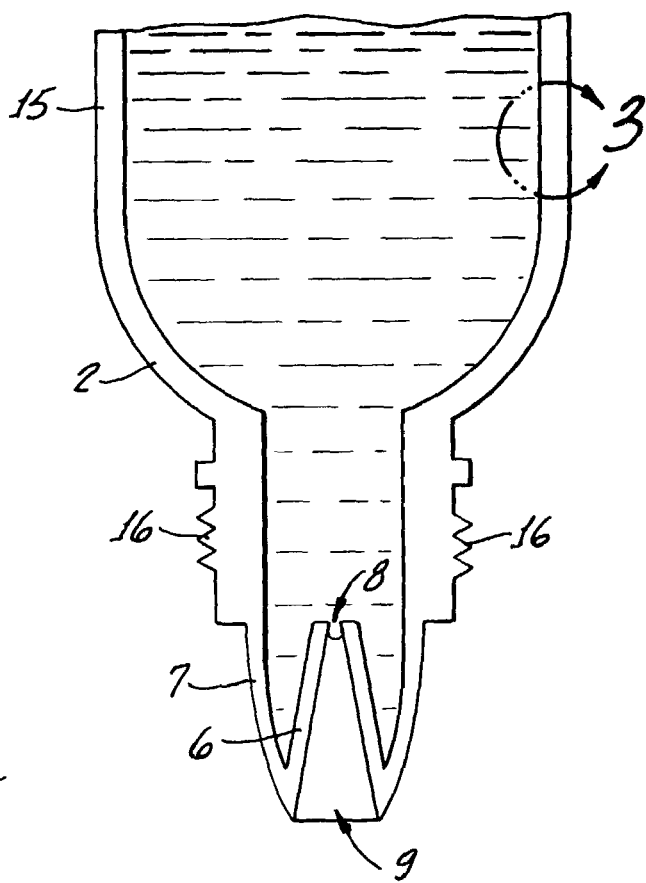
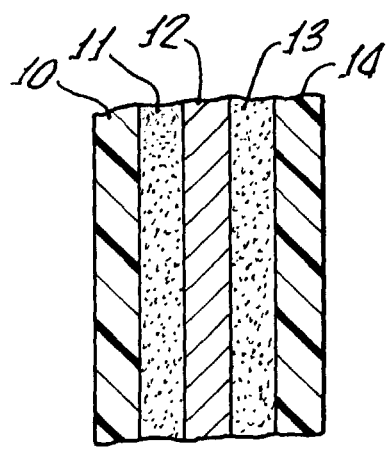

CONTROLLED DROP DISPENSING CONTAINER

BACKGROUND OF THE INVENTION

1. Field of the Invention

This invention relates to packaging materials for pharmaceutical preparations. More particularly, this invention relates to dispensing containers for multi-use ophthalmic liquids.

2. Description of Related Art

Ophthalmic liquids are currently dispensed into the eye using a standard polyethylene bottle, a dispensing tip and cap. The standard ophthalmic bottle, a readily available polyethylene bottle, has a major shortcoming in that it is subject to significant loss of water over time. This evaporation increases the concentration of the solution making it prematurely useless because the solution becomes too concentrated for ophthalmic use before the useful life of the active materials has elapsed. This is particularly problematic for ophthalmic solutions since they tend to have relatively small volumes, which make the samples even more susceptible to evaporation due to the greater surface area to volume ratio. This significant reduction in shelf life causes significant waste of the ophthalmic solution at significant cost to the manufacturer or possibly the patient. Another shortcoming of the current packaging is that the polyethylene is not as pliable as would be desired, giving less than optimal control of the drop size.

SUMMARY OF THE INVENTION

These obstacles are overcome in the present invention by substituting the standard ophthalmic bottle with a laminate tube that has a dispensing tip. Laminate tubes suffer significantly less water loss than the standard ophthalmic bottles due to the presence of a barrier layer, through which water is significantly less permeable compared to polyethylene or another similar polymeric material. The dispensing tip is joined to the laminate tube via a shoulder. A preferred embodiment of this invention also comprises a cap, which has a reusable seal between the cap and the dispensing tip. Another preferred embodiment of this invention also comprises a tamper evident tear strip.

In another embodiment of this invention, certain methods of using the controlled drop dispensing container are novel and non-obvious.

BRIEF DESCRIPTION OF THE DRAWING FIGURES

FIG. 1 is an exterior view of the controlled drop dispensing container of the invention 1, including a laminate tube 15, shoulder 2, dispensing tip 7, and cap 4, a reusable seal 3 between the dispensing tip 7 and the cap 4, with a cross sectional view of the cap 4.

FIG. 2 is a cross sectional view of part of the laminate tube 15, the shoulder 2, and the dispensing tip 7.

FIG. 3 is a cross sectional view of the laminate material used to fabricate the laminate tube 15.

DETAILED DESCRIPTION OF THE INVENTION

FIG. 1 is a general view of a preferred embodiment of this invention comprising the laminate tube 15 connected to the shoulder 2, which is connected to the dispensing tip 7. In a preferred embodiment of this invention, the controlled drop dispensing container comprises a cap 4. While not intending to limit the scope of the invention, the cap 4 can be formed by injection molding and is generally comprised of a polymeric material. In the preferred embodiment of this invention, the cap 4 is comprised of polystyrene or polypropylene. In another preferred embodiment of this invention a reusable seal 3 is formed between the cap 4 and the dispensing tip 7. In a preferred embodiment of the invention, the reusable seal 3 is secured by a male thread 16 on the tip and a female thread 17 in the cap 4. In another preferred embodiment of the invention the cap 4 and the dispensing tip 7 may snap together to secure the seal. However, a person skilled in the art will recognize that there other ways to form and secure a reusable seal 3 without departing from the scope and spirit of the invention. In another preferred embodiment of the invention, the cap 4 further comprises a tamper evident tear strip 5, as depicted in FIG. 1. The use of a tamper evident tear strip 5 confers an additional advantage to this invention in that it eliminates the need for a separate tamper evident seal. A tamper evident tear strip 5 is a strip of material connecting the shoulder 2 or dispensing tip 7 and the cap 4 in such a way that it prevents the cap 4 from being removed without damaging the strip, thus alerting the user that the tube has been tampered with. While not intending to the limit the scope of the invention, the tamper evident strip could be comprised of the same material as the cap 4, and could be formed with the cap 4 in an injection molding process. For example, the tamper evident tear strip 5 could be designed in such a way that it is attached to the cap 4 and could be twisted onto the tip when packaging the product without being damaged, but the cap and tamper evident tear strip could not be twisted in the opposite direction so as to open the reusable seal 3 without being damaged in a way that is obvious to the user.

FIG. 2 is a cross sectional view of part of the controlled drop dispensing container 1 showing the upper portion of laminate tube 15, the shoulder 2, and the dispensing tip 7. While not intending to limit the scope of the invention in any way, the dispensing tip 7 can be formed by injection molding. The dispensing tip 7 comprises two orifices, the inner orifice 8 and outer orifice 9. The inner orifice 8, which is the smaller of the two orifices, is sized to control the flow of the liquid for effective use. The outer orifice 9, which is the larger of the two orifices, is sized to control the size of the drop for effective use. The two orifices are in fluid communication so that the liquid flows through the inner orifice 8 to the outer orifice 9, and the drop forms on the outside of the outer orifice 9 for administration of the liquid contents of the controlled drop dispensing container. The two orifices can be coupled by any of a number of means, which would be obvious to those skilled in the art. In FIG. 2, the two orifices are coupled via a chamber that forms an inverted cone 6. However, those skilled in the art will recognize that there are numerous other ways the two orifices could be coupled. While not intending to limit the scope of the invention in any way, the two orifices could, for example, be connected by a cylindrically shaped chamber, where one end of the cylinder has a wall surrounding the inner orifice 8 and the other end comprises the outer orifice 9. In fact, a chamber of any shape could be suitable as long as the inner orifice 8 is used to regulate the flow of the liquid and the outer orifice 9 is used to control the drop size. In the preferred embodiment of the invention, the means of coupling the inner orifice to the outer is a chamber which forms an inverted cone. While the dispensing tip 7 may be comprised of any suitable material known to those skilled in the art, in the preferred embodiment of this invention the dispensing tip 7 is comprised of polyethylene or polypropylene.

As seen in FIG. 2, the laminate tube 15 is connected to the dispensing tip 7 via a shoulder 2. The process of connecting a laminate tube 15 to a dispensing tip 7 via a shoulder 2 could be readily carried out by those skilled in the art without undue experimentation, and a skilled person would recognize that there are a number of ways this could be done without departing from the scope and spirit of the invention. While not intending the limit the scope of this invention, the dispensing tip 7 and shoulder 2 could be formed simultaneously in one injection molding process. In this process the tube is held vertically in a press and an injection mold is brought in under the tube to form the dispensing tip 7 at the bottom of the tube. The bottom of the press is slightly rounded to form the shoulder 2, and the molten polymer of the shoulder 2 bonds to the inside of the laminate tube 15. While not intending to limit the scope of the invention in any way, the shoulder 2 is typically made of the same polymeric material as the dispensing tip 7. In the preferred embodiment of this invention, the shoulder 2 is comprised of polyethylene or polypropylene. Although the tip 7 and shoulder 2 can be prepared in the previously described injection molding process, this process is described purely for illustration purposes. Those skilled in the art will recognize that there are other embodiments prepared by alternative methods known in the art that would fall within the spirit and scope of this invention. For example, the dispensing tip 7 could be formed separately and press fit into the shoulder 2 in a number of different ways.

Laminate tubes are well known in the art, and commercially available from companies such as CCL Plastic Packaging, headquartered in Los Angeles, Calif., and Montebello Packaging, Inc., of Oak Park, Ill. Turning to FIG. 3, the laminate tube 15 is comprised of five layers as shown or may comprise three layers: an outer polymeric layer 10, an optional first tie layer 11, a middle barrier layer 12, an optional second tie layer 13, and an inner polymeric layer 14. The outer polymeric layer 10 and the inner polymeric layer 14 form the outside and inside surfaces of the laminate tube 1, respectively. The barrier layer is sandwiched between the inner polymeric layer 14 and outer polymer layer 10 and bonded to the two polymeric layers by the optional tie layers. The inner polymeric layer 14 and the outer polymeric layer 10 may be the same or different, and could be comprised of any suitable polymer. In a preferred embodiment of this invention, the inner polymeric layer 14 comprises polyethylene and the outer polymeric layer 10 comprises polyethylene or polyester. In a more preferred embodiment of this invention, the outer polymeric layer 10 comprises polyethylene. The barrier layer is comprised of any material with sufficient impermeability of water and physical flexibility to be useful in this invention. While not wishing to limit the scope of the invention in any way, examples of suitable barrier layer 12 materials are aluminum foil, silicon dioxide, and foils of individual metals or alloys. Preferably, the barrier layer 12 comprises aluminum foil. The first tie layer 11 and the second tie layer 13 are optional, and if they are not present, heat treatment or some equivalent process is used to bond the barrier layer to the inner and outer polymeric layers. The first tie layer 11 and the second tie layer 13 may be the same or different, and comprise any material capable of bonding the barrier layer to the inner or outer polymeric layers.

The laminate tube 15 is formed by rolling a sheet of the laminate material into a tube, which is welded together by heat. While not intending to limit the scope of the invention in any way, this can be done by rolling the laminate sheet into a tube and pressing together the edges of the sheet to be sealed using an iron on the inside of the tube and an anvil on the outside of the tube. The end of the tube which does not contain the tip is closed by heat sealing as well. While not intending to limit the scope of the invention, this can be done by heating the inside or outside of the end of the tube and pressing it together.

In a preferred embodiment of this invention, the controlled drop dispensing container 1 contains a liquid. In a more preferred embodiment of this invention, the liquid contained in the controlled drop dispensing container 1 is an ophthalmic liquid, an aural preparation (ear medication), or a liquid used for the care and cleaning of contact lenses. In the most preferred embodiment of this invention, the liquid contained in the controlled drop dispensing container 1 is an ophthalmic liquid.

In another embodiment of this invention, the controlled drop dispensing container 1 is used for controlled dispensing of any liquid. Controlled dispensing is dispensing in which individual drops of a liquid are formed. In the preferred embodiment of this invention, the controlled drop dispensing container 1 is used to dispense an ophthalmic liquid, an aural preparation (ear drops), or a liquid used for the care and cleaning of contact lenses. In the most preferred embodiment of this invention, the controlled drop dispensing container 1 is used to dispense an ophthalmic liquid. The best mode of using the controlled drop dispensing container 1 is embodied in the following example.

To a controlled drop dispensing container 1 having a volume of 2 mL, is added 0.5 mL of Alphagan® brimonidine ophthalmic solution, available from Allergan, Inc., Irvine, Calif., which contains 0.2% bromonidine tartrate dissolved in water. A cap 4 is securely fastened to the dispensing tip 7, such that the reusable seal 3 is formed. After three months, the solution is tested and the brimonidine tartrate concentration is unchanged. A controlled amount of the solution is then administered to the eye of a patient suffering from a condition that is treated with brimonidine tartrate.

What is claimed is:

1. A controlled drop dispensing container comprising:
   an aqueous ophthalmic liquid,
   a dispensing tip comprising:
   a. an inner orifice having a diameter sufficiently small to restrict the flow of a liquid to the desired rate,
   b. an outer orifice having a diameter larger than the inner orifice and sufficiently large to form a drop of a liquid of the desired size, and
   c. a means of coupling the inner orifice to the outer orifice such that a liquid can flow through the inner orifice to the outer orifice; and
   a laminate tube connected to the dispensing tip comprising:
   a. an outer polymeric layer,
   b. a middle barrier layer,
   c. an inner polymeric layer, and
   d. a shoulder connecting the laminate tube to the dispensing tip.

2. The controlled drop dispensing container of claim 1 wherein the laminate tube comprises two tie layers, wherein one tie layer is between the outer polymeric layer and the barrier layer, and wherein another tie layer is between the inner polymeric layer and the barrier layer.

3. The controlled drop dispensing container according to claim 1 which further comprises a cap and a reusable seal between the cap and the dispensing tip.

4. The controlled drop dispensing container according to claim 3 wherein the reusable seal between the cap and the dispensing tip is secured by a male thread on the dispensing tip that matches a female thread in the cap.

5. The controlled drop dispensing container according to claim 3 wherein the cap and the dispensing tip snap together to secure the reusable seal.

6. The controlled drop dispensing container according to claim 3 wherein the cap further comprises a tamper evident tear strip.

7. The controlled drop dispensing container according to claim 3 in which the barrier layer is a metal foil or $SiO_2$, the inner polymeric layer comprises polyethylene, the outer polymeric layer comprises polyethylene or polyester, the shoulder is comprised of polyethylene or polypropylene, the dispensing tip is comprised of polyethylene or polypropylene, and the cap is comprised of polystyrene or polypropylene.

8. The controlled drop dispensing container according to claim 3 in which the barrier layer is a metal foil or $SiO_2$, the inner polymeric layer comprises polyethylene, the outer polymeric layer comprises polyethylene or polyester, the shoulder is comprised of polyethylene or polypropylene, the dispensing tip is comprised of polyethylene or polypropylene, and the cap is comprised of polystyrene or polypropylene.

9. The controlled drop dispensing container according to claim 8 wherein said means of coupling the inner orifice to the outer orifice comprises a chamber that forms an inverted cone.

10. The controlled drop dispensing container according to claim 9 in which the barrier layer is aluminum foil.

11. The controlled drop dispensing container according to claim 10 in which the outer polymeric layer is polyethylene.

12. A method of dispensing a liquid dropwise from a controlled drop dispensing container, said control drop dispensing container comprising:
  a laminate tube comprising:
    a. an outer polymeric layer,
    b. a middle barrier layer,
    c. an inner polymeric layer, and
    d. a shoulder connecting the laminate tube to a dispensing tip;
  the dispensing tip comprising:
    a. an inner orifice having a diameter sufficiently small to restrict the flow of said liquid to the desired rate,
    b. an outer orifice having a diameter larger than the inner orifice and sufficiently large to form a drop of the desired size from said liquid, and
    c. a means of coupling the inner orifice to the outer orifice such that said liquid flows through the inner orifice to the outer orifice;
wherein said method comprises passing the liquid sequentially from said laminate tube past the shoulder and through the inner orifice and the outer orifice to be dispensed as individual drops, and wherein said liquid is an aqueous ophthalmic liquid.

13. The method of claim 12 wherein the controlled drop dispensing container further comprises a cap and a reusable seal between the cap and the dispensing tip.

\* \* \* \* \*

UNITED STATES PATENT AND TRADEMARK OFFICE
CERTIFICATE OF CORRECTION

| | | |
|---|---|---|
| PATENT NO. | : 8,403,176 B2 | Page 1 of 1 |
| APPLICATION NO. | : 10/349572 | |
| DATED | : March 26, 2013 | |
| INVENTOR(S) | : Scott J. Gerondale | |

It is certified that error appears in the above-identified patent and that said Letters Patent is hereby corrected as shown below:

In the Specification

In column 4, line 28, delete "bromonidine" and insert -- brimonidine --, therefor.

Signed and Sealed this
Seventh Day of October, 2014

Michelle K. Lee
*Deputy Director of the United States Patent and Trademark Office*